United States Patent
Gottlieb et al.

(10) Patent No.: US 8,834,160 B1
(45) Date of Patent: Sep. 16, 2014

(54) DENTAL WEDGE AND FORMER DEVICE

(76) Inventors: Marc Gottlieb, Levittown, NY (US); Craig Bruns, San Ramon, CA (US)

( * ) Notice: Subject to any disclaimer, the term of this patent is extended or adjusted under 35 U.S.C. 154(b) by 106 days.

(21) Appl. No.: 13/317,071

(22) Filed: Oct. 7, 2011

Related U.S. Application Data

(60) Provisional application No. 61/404,762, filed on Oct. 8, 2010.

(51) Int. Cl.
*A61C 7/00* (2006.01)

(52) U.S. Cl.
USPC .......................................................... 433/149

(58) Field of Classification Search
USPC .................... 433/39–40, 147–149, 215, 216, 433/139–140; 132/321–329
See application file for complete search history.

(56) References Cited

U.S. PATENT DOCUMENTS

| | | | |
|---|---|---|---|
| 552,697 A * | 1/1896 | Peterson | 433/39 |
| 701,799 A * | 6/1902 | Crenshaw | 433/39 |
| 2,090,904 A | 8/1937 | Singer | |
| 3,815,243 A * | 6/1974 | Eames | 433/149 |
| 3,890,714 A | 6/1975 | Gores | |
| 4,259,070 A | 3/1981 | Soelberg et al. | |
| 4,578,035 A | 3/1986 | Pruitt | |
| 6,234,793 B1 * | 5/2001 | Brattesani et al. | 433/39 |
| 7,077,651 B2 * | 7/2006 | Anderson | 433/139 |
| 7,083,412 B1 * | 8/2006 | Karapetyan | 433/148 |
| 7,976,308 B2 * | 7/2011 | Hegedus | 433/149 |
| 2005/0089813 A1 | 4/2005 | Slone | |
| 2005/0118554 A1 | 6/2005 | Kilcher et al. | |
| 2008/0064000 A1 | 3/2008 | Clark | |
| 2008/0064002 A1 | 3/2008 | Clark | |
| 2008/0064003 A1 | 3/2008 | Clark | |
| 2008/0064004 A1 | 3/2008 | Clark | |
| 2008/0064009 A1 | 3/2008 | Clark | |
| 2008/0064012 A1 | 3/2008 | Clark | |

* cited by examiner

*Primary Examiner* — Yogesh Patel
(74) *Attorney, Agent, or Firm* — Theodore J. Bielen, Jr.

(57) ABSTRACT

A dental wedge and forming device utilizing a unitary body having a pair of wings which are intended to lie against the outer surfaces of adjacent teeth, either on the lingual or buccal region of the teeth. A curved nose is constructed to extend between the adjacent teeth and includes a flat side and an opposite radiused side. A pair of the devices are nested in opposition in order to hold a dental matrix band in place about a prepared tooth, thus allowing a dental practitioner to practice proper biomimetic restorative techniques.

7 Claims, 3 Drawing Sheets

DENTAL WEDGE AND FORMER DEVICE

CROSS-REFERENCE TO RELATED APPLICATION

The application claims the benefit, under 35 U.S.C. §119(e), of U.S. Provisional Patent Application No. 61/404,762 filed on 8 Oct. 2010, which is incorporated herein, by reference, in its entirety.

BACKGROUND OF THE INVENTION

The present invention relates to a novel and useful dental wedge and former device which is used in conjunction with dental restoration techniques.

The treatment of interproximal cavities requires the dental practitioner to remove decayed enamel and dentin along the side or proximal wall of a tooth which is nested adjacent, and often contacts, healthy tooth. In general, a matrix band is placed around the tooth in order to confine the filling materials to the removed portion of the tooth which is to be filled. At this point, dental wedges are normally are used to spread adjacent teeth and to stabilize the matrix band. In addition, a dental separator ring may also be employed to apply pressure to further separate adjacent proximal teeth and to tighten the positioning of the dental matrix band, thus, augmenting the force applied by a dental wedge.

Unfortunately, in the past, wedges and dental separator rings have caused the collapse of the matrix band and created gaps between the matrix band and the tooth being restored. Collapse of the matrix band does not allow a proper formation or morphology of restorative material in the tooth. Gaps in the matrix band also permit restorative material to flow outside the confines of the matrix band creating a "flash", which is highly undesirable. The latter problem is especially acute when composite material is used to create the dental restoration.

In the past, many structures have been proposed as dental wedges to aid in dental filling and restorative methods. For example, U.S. Pat. No. 4,578,035 describes a dental wedge formed by two flexible members, both of which are triangular in cross-section. The two members are connected to form a closed loop to fill the embrasures between adjacent teeth.

U.S. Pat. No. 2,090,904 illustrates a dental matrix which is placed between the teeth and includes a web that fills the space between the teeth and side portions and that extends along the outer surfaces of the teeth at the lingual and buccal sides, thereof.

U.S. Pat. Nos. 3,890,714 and 7,083,412 show dental wedges which include elongated members that are singly forced between adjacent teeth to separate the same. The members are triangular or circular in cross-sectional configuration.

U.S. Pat. No. 4,259,070 and United States Patent Application Publication 2005/0089813 teach dental wedges which are formed into portions that interfit with respect to one another in order to separate teeth as a portion of a dental restorative system.

United States Patent Application Publication 2005/0118554 describes a system for separating teeth in preparation for a dental restoration that includes a pair of wedge elements that abut one another between the teeth.

United States Patent Application Publication 2008/0006400, 2008/0064002, 2008/0064003, 2008/0064004, 2008/0064009, 2008/0064012 show a dental wedge which utilizes a single piece member that is forced downwardly between adjacent teeth to separate the same. The single piece member includes a narrow middle section and a forked end portion which are separable to create a cavity for a dental ring.

A dental wedge device which is capable of positioning and efficiently sealing a dental matrix band for dental restorative work would be a notable advance in the field of dentistry.

SUMMARY OF THE INVENTION

In accordance with the present invention a novel and useful dental wedge and forming device is herein provided.

The wedge of the present invention is formed with a pair of flanges, ears, or wings which are curved and merge into an elongated element or nose which is curved. The meeting place between the pair of wings creates a recess or cusp which serves as a pressing place for a dental contact ring. The wedge of the present invention may be formed of any pliable material such as polymeric plastic and the like.

The elongated element or nose of the wedge of the present invention possesses a curve which allows the nose to conform to the outer surface of a matrix band lying in an embrasure and against the proximal wall of a tooth being restored. In addition, the dental wedge of the present invention, when used in combination with a like device, forms an interacting pair that slide adjacent to one another to increase the wedging force against the matrix band in the embrasure. The curved elongated element also serves to direct the side-by-side orientation of identical wedge devices of the present invention when in use. In addition, the elongated element of the dental wedge of the present invention efficiently seals the dental matrix band to the proximal surface of the tooth to prevent escape of filling material, such as composites. Likewise, the wedging afforded by a pair of devices of the present invention is maintained by the use of a dental separator or sectional ring. The wedge of the present invention also functions to space the dental separator ring from the tooth to provide an increased visual field to the dental practitioner performing the restorative technique. It should also be noted, that the elongated element or nose of the dental wedge of the present invention, when viewed in section, includes a flattened surface intended to contact a flatten surface of a similar device, and a concave curved or rounded surface intended to contact the dental matrix band. The latter concave surface seals the floor of the preparation at the base of the dental matrix band.

It should also be seen, that a curve may be formed in the flange or ears of the wedge device of the present invention in order to capture the tip of the elongated member after it passes through space between the teeth. In this manner, the end portion of the wedge gives further support to the matrix band outside the buccal or lingual embrasure. The curvature of the ears of the wedge device also support the matrix band when the decay region of the tooth extends beyond the teeth contact area i.e. to the lingual or buccal walls thereof. Thus, the wedge device achieves normal rounded contours in the restoration. Moreover, an extension or fin maybe formed into the nose of the wedge of the present invention to further seal the floor of the matrix band against a concavity in the tooth root below a proximal box form created by a dental practitioner.

Further, the wedge device of the present invention may be used in pairs, each of a different size to accommodate odd-shaped or rotated teeth.

It may be apparent that a novel and useful dental wedge and forming device has been hereinabove described.

It is therefore an object of the present invention to provide a dental wedge and forming device which supports a matrix band used in dental restorative procedures.

Another object of the present invention is to provide a dental wedge and forming device which prevents collapse or crushing of the dental matrix band by a separator or sectional ring used to separate adjacent teeth.

A further object of the present invention is to provide a dental wedge and forming device which may be used with a fashioned box form, to seal the floor portion of the dental matrix band during restorative procedures, and to provide a pressure place for the dental separator ring without disrupting the sealing of the dental matrix band by the wedge of the present invention.

A further object of the present invention is to provide a dental wedge and forming device which may be used with a like device and includes an elongated portion that is curved and includes a concave surface that conform to the outer surface of the dental matrix band, as well as an opposite flattened surface to allow and enhance sliding engagement between the elongated elements of like wedges.

A further object of the present invention is to provide a dental wedge and forming device which may be placed into the buccal or lingual embrasure and is capable of sealing a dental matrix adjacent the buccal and lingual tooth walls at the gingival floor.

Yet another object of the present invention is to provide a dental wedge device which is compatible with composite filling material used in a dental restoration.

Another object of the present invention is to provide a dental wedge device which may be used in pairs having different scales to accommodate odd-shaped or rotated teeth in dental restoration procedures.

Yet another object of the present invention is to provide a former for composite filling material used in dental restorations in order to create biomimetic teeth walls in place of teeth walls destroyed by decay.

Another object of the present invention is to provide a dental wedge and forming device which avoids the formation of a dental restoration morphology that is grossly distorted in size and shape, requiring excessive finishing by a dental practitioner to produce a natural morphology.

The invention possesses other objects and advantages especially as concerns particular characteristics and features thereof which will be discussed as the specification continues.

Figure 1:
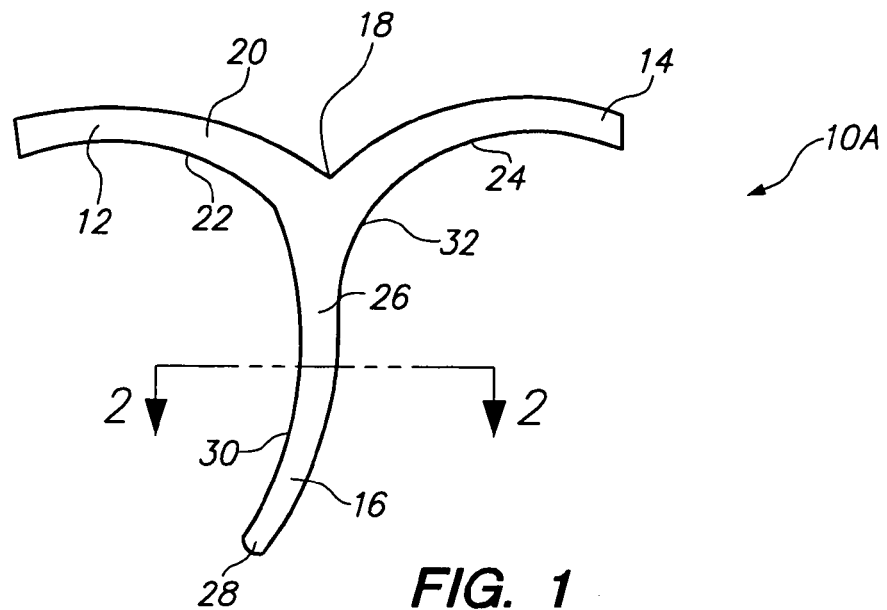
FIG. 1 is a top plan view of the device of the present invention.

For a better understanding of the invention reference is made to the following detailed description of the preferred embodiments of the invention which should be taken in conjunction with the above described drawings.

DETAILED DESCRIPTION OF THE PREFERRED EMBODIMENTS OF THE INVENTION

Various aspects of the present invention will evolve from the following detailed description of the preferred embodiments thereof which should be referenced to the prior described drawings.

An embodiment of the invention is depicted by reference character 10, followed by an uppercase letter to denote variations thereof. With respect to FIG. 1, an embodiment of a dental wedge and former 10A is shown. Device 10A includes as one of its elements ears, wings, or flanges 12 and 14 which converge or "y" into a downwardly projecting elongated element or nose 16 when viewed from its side, FIG. 4. Wings 12 and 14 converge at a cusp or recess 18, the purpose in which will be discussed hereinafter. Also, wings 12 and 14 include an upper surface 20, above lower surface 34, defining the height of wings 12 and 14. Wings or flanges 12 and 14 possess curved or concave surfaces 22 and 24, respectively. Wedge 10A may be formed of polymeric material.

Figure 2:
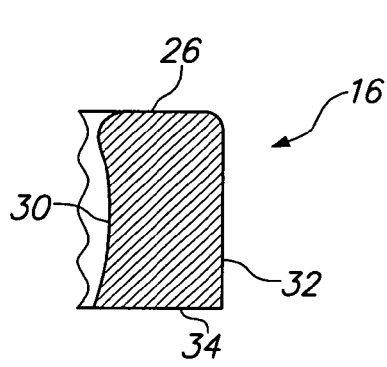
FIG. 2 is a sectional view taken along line 2-2 of FIG. 1.
Figure 4:
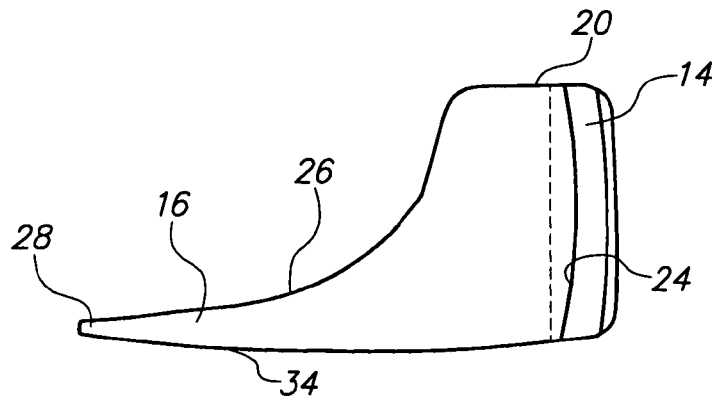
FIG. 4 is a right side elevational view of the device of the present invention.

Nose or elongated member 16 of device 10A, FIG. 1, includes a sloping upper surface 26, best shown in FIG. 4, which narrows to a tip 28, which is of a lesser height than wings 12 and 14. Nose 16 also curves, generally from wing 14 toward wing 12, in plan view, FIG. 1. Thus, tip 28 is biased toward wing 12 relative to centrally located cusp 18, FIG. 1. It should also be realized that nose 16 includes a concave surface 30 and an opposite convex surface 32, in plan view, FIG. 1. As depicted in FIG. 2, surface 30 is formed as a curved or undercut structure between upper surface 26 and lower or undersurface 34, thereof, when viewed in section. On the other hand, surface 32 is generally flat, in section.

Figure 3:
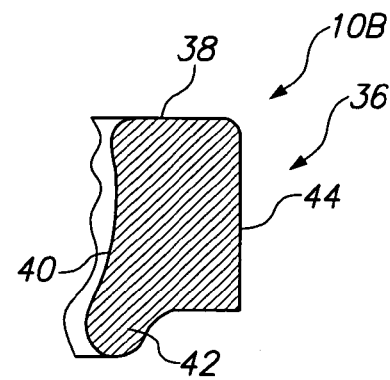
FIG. 3 is a sectional view similar to that of FIG. 2, showing a variation of the cross-sectional configuration of the elongated element of the device of the present invention.

FIG. 3, represents an alternative nose structure 36 for device 10B in which an upper surface 38 is generally flat while undercut or concave surface 40, in section, includes an appendage or rudder 42 which is intended to better apply device 10B during certain restoration preparations requiring lower wedge support. Convex surface 44 is generally flat, in section, between upper surface 38 and in the vicinity rudder 42.

Figure 5:
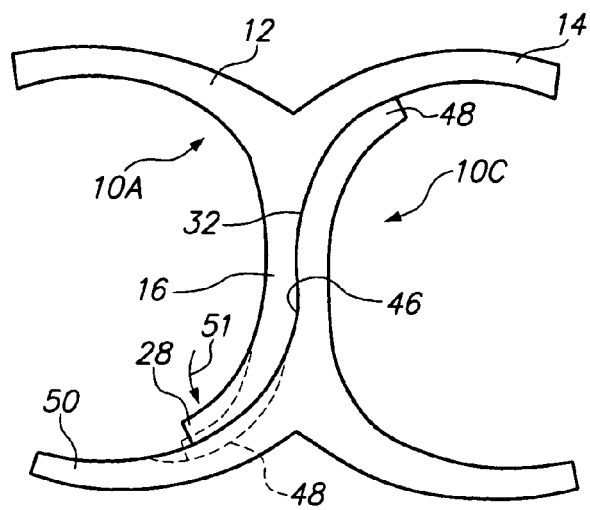
FIG. 5 is a top plan schematic view of a pair of nested devices of the present invention and also denoting a variation of the same.

Turning now to FIG. 5, it may be observed that a pair of devices of nearly identical configuration are shown nested to one another, 10A and 10C. The curve of nose 16 serves as guide for such nesting. It may be seen, flattened surface 32, in section, of nose 16 of device 10A fits snuggly against flattened surface 46, in section, of nose 48 of device 10C. However, device 10B includes an optional groove 48 of wing 50 which serves as an insertion cavity for the tip 28 and the ajoining portion of tip 28 of nose 16, directional arrow 51. The arrangement of devices 10A and 10C in FIG. 5 represents the general positioning a pair of devices 10A and 10C, or a pair of identical devices 10A, when used in a dental preparation associated with restoration procedures depicted in FIG. 6. Devices similar to wedge and former device 10A may be employed in different sizes, scaled up or down, to accommodate odd-shaped or rotated teeth.

Figure 6:
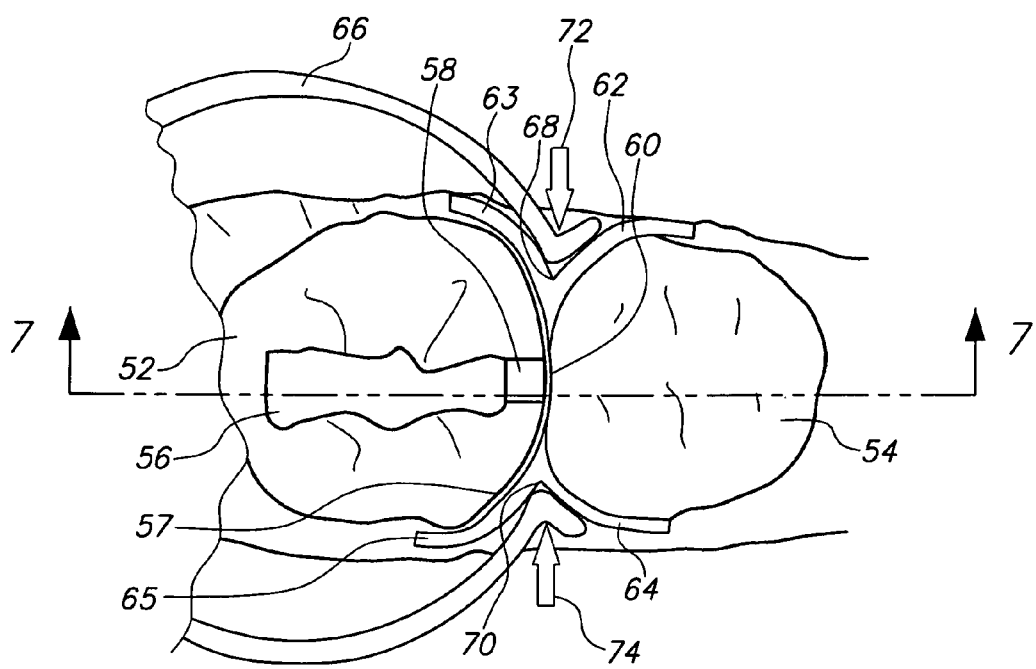
FIG. 6 is a top plan view of a pair of identical devices of the present invention in place adjacent a dental matrix band and being employed with a dental separator ring.
Figure 7:
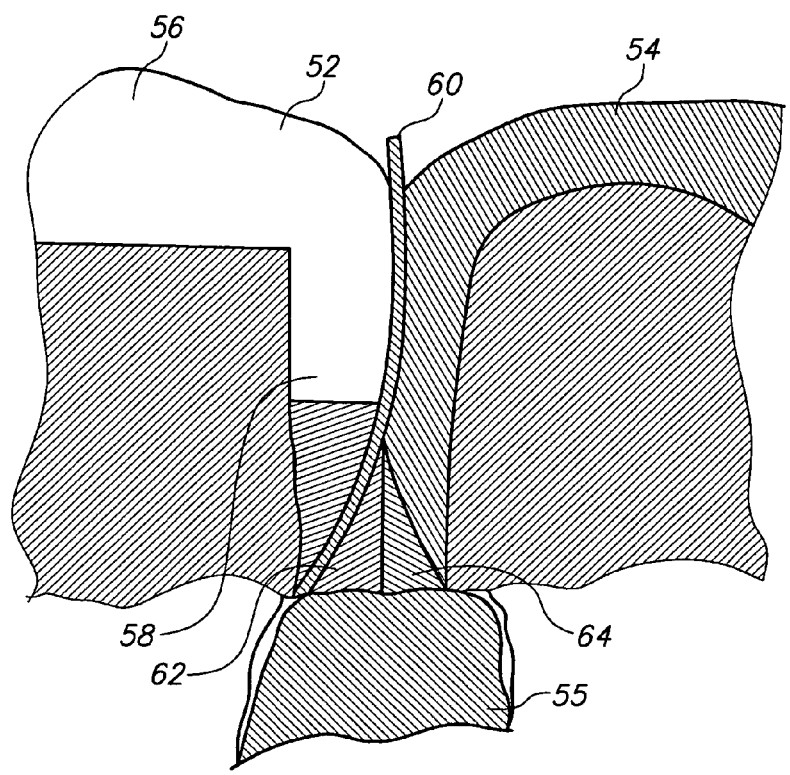
FIG. 7 is a schematic sectional view taken along line 7-7 of FIG. 6.

In operation, FIGS. 6 and 7 shows a pair of teeth 52 and 54 above papillae 55 in preparation for the reception of flowable and packable composite filling material during a dental restoration. Tooth 52 appears with dentin having been removed from area 56 and 58, the latter being depicting in a "box" form, which necessarily includes removal of a portion of the proximal wall 57 of tooth 52. A matrix band 60 has been positioned against tooth 52, and between teeth 52 and 54, specifically adjacent dentin voided area 56 and box form area 58. A pair of wedge and former devices 62 and 64, each being identical to wedge 10A of FIG. 1, have been inserted between teeth 52 and 54, wedge and former device 62, on the lingual side of teeth 52 and 54, lies snuggly against matrix band 60. Wedge and former device 64, inserted from the buccal side, lies against device 62 to create further sealing pressure against matrix band 60, similar to the format depicted in FIG. 5. Wing 63 of device 62 and wing 65 of device 64 also support matrix band 60. Dental separator ring. 66 has been placed in the cusps 68 and 70 of wedge and former devices 62 and 64, respectively, to create a squeezing force represented by directional arrows 72 and 74. The upshot of the arrangement depicted in FIG. 6, is to position devices 62 and 64 to firmly seal matrix band 60 (without collapse) against tooth 52 to allow the proper application of composite filling material in dentin voided areas 56 and 58 of tooth 52 without escape therefrom. It should also be realized that another ring may be employed on the other side of tooth 52 when the restoration procedure extends thereto.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A dental wedge device configured to be positioned between a first tooth and an adjacent second tooth, at least one of the first and second teeth having a matrix band, comprising:
   a. a curved elongated member extending along a dimension of elongation, said curved elongated member including at least a first concave surface and an opposite flattened surface, transverse to said dimension of elongation;
   b. a first wing having a certain height, said first wing having a direct connection to said curved elongated member; and
   c. a second wing having a certain height, said second wing having a direct connection to said curved elongated member at said connection of said first wing to said curved elongated member, said curved elongated member sloping outwardly from said connections of said first and second wings and terminating in a tip of lesser height than said certain heights of said first and second wings.

2. The device of claim 1 in which said first and second wings each possess a curved surface.

3. The device of claim 2 which additionally comprises a recess in the vicinity of said direct connections of said first and second wings to said curved elongated member.

4. The device of claim 2 which additionally comprises an appendage extending from said curved elongated member, apart from said tip.

5. The device of claim 1 which additionally comprises a recess in the vicinity of said direct connections of said first and second wings to said curved elongated member.

6. The dental wedge device of claim 5 in which said dental wedge device comprises a first dental wedge device and which further comprises, in combination, a second dental wedge device, said second dental wedge comprising:
   a. a curved elongated member extending along a dimension of elongation, said curved elongated member including at least a first concave surface and an opposite flattened surface, transverse to said dimension of elongation;
   b. a first wing having a certain height, said first wing having a direct connection to said curved elongated member; and
   c. a second wing having a certain height, said second wing having a direct connection to said curved elongated member at said connection of said first wing to said curved elongated member, said curved elongated member sloping outwardly from said connections of said first and second wings and terminating in a tip of lesser height than said certain heights of said first and second wings, and having a recess in the vicinity of said direct connections of said first and second wings, and, further, in combination; and
   d. a dental separator for exerting a force at said recess of said first device and at a recess of said second device.

7. The device of claim 1 which additionally comprises an appendage extending from said curved elongated member, apart from said tip.

* * * * *